(12) United States Patent
Shivdasani et al.

(10) Patent No.: US 9,192,765 B2
(45) Date of Patent: Nov. 24, 2015

(54) METHOD AND APPARATUS FOR STIMULATING RETINAL NERVE CELLS

(75) Inventors: Mohit Naresh Shivdasani, East Melbourne (AU); Christopher Edward Williams, East Melbourne (AU); Peter John Blamey, East Melbourne (AU)

(73) Assignee: The Bionics Institute of Australia (AU)

( * ) Notice: Subject to any disclaimer, the term of this patent is extended or adjusted under 35 U.S.C. 154(b) by 283 days.

(21) Appl. No.: 13/516,752

(22) PCT Filed: Dec. 2, 2010

(86) PCT No.: PCT/AU2010/001637
§ 371 (c)(1),
(2), (4) Date: Sep. 28, 2012

(87) PCT Pub. No.: WO2011/072322
PCT Pub. Date: Jun. 23, 2011

(65) Prior Publication Data
US 2013/0066397 A1 Mar. 14, 2013

(30) Foreign Application Priority Data
Dec. 18, 2009 (AU) ................................ 2009906151

(51) Int. Cl.
*A61N 1/36* (2006.01)
*G09B 21/00* (2006.01)
*A61N 1/05* (2006.01)

(52) U.S. Cl.
CPC .......... *A61N 1/36046* (2013.01); *G09B 21/008* (2013.01); *A61N 1/0543* (2013.01)

(58) Field of Classification Search
CPC ............ A61N 1/36046; A61N 1/0543; A61N 1/0551; A61N 1/36017; A61N 1/025; A61N 1/05; A61F 9/08; A61F 2/14; A61B 2562/02; A61B 5/6867; G06K 9/605
USPC ............................... 607/1–2, 53–54, 115–116
See application file for complete search history.

(56) References Cited

U.S. PATENT DOCUMENTS

| | | | |
|---|---|---|---|
| 6,920,358 B2* | 7/2005 | Greenberg et al. | 607/54 |
| 7,403,822 B2* | 7/2008 | Tano et al. | 607/53 |
| 8,700,166 B2* | 4/2014 | Sarpeshkar et al. | 607/53 |
| 2002/0010496 A1 | 1/2002 | Greenberg et al. | |
| 2002/0091421 A1 | 7/2002 | Greenberg et al. | |
| 2006/0074461 A1 | 4/2006 | Tano et al. | |

(Continued)

FOREIGN PATENT DOCUMENTS

WO WO-2007/127444 A2 11/2007

OTHER PUBLICATIONS

"International Application No. PCT/AU2010/001637, International Search Report and Written Opinion mailed Mar. 15, 2011", 11 pgs.

(Continued)

*Primary Examiner* — Deborah Malamud
(74) *Attorney, Agent, or Firm* — Schwegman Lundberg & Woessner, P.A.

(57) ABSTRACT

A method and apparatus is described for electrically stimulating a patient's retina with an electrode array (32) implanted in the patient's eye, wherein one or more images are captured; at least one line and/or edge in the images is determined (21), a line of electrodes in the electrode array corresponding to a detected line and/or edge is identified (24); and electrical current is applied simultaneously to electrodes of the identified line of electrodes.

9 Claims, 8 Drawing Sheets

(56) References Cited

U.S. PATENT DOCUMENTS

| 2006/0241753 | A1 | 10/2006 | Suaning et al. |
| 2008/0046030 | A1 | 2/2008 | Greenberg et al. |
| 2008/0058897 | A1 | 3/2008 | McMahon et al. |
| 2008/0228242 | A1 | 9/2008 | Fink et al. |

OTHER PUBLICATIONS

Elfar, Sylvia D., et al,, "A cortical (V1) neurophysiological recording model for assessing the efficacy of retinal visual prostheses", J Neurosci Methods (2009), doi:10.1016/j.jneumeth.2009.02.019, (Feb. 25, 2009), 13 pgs.

Horsager, A., et al., "Spatiotemporal interactions in retinal prosthesis subjects", IOVS Papers in Press, published on Sep. 9, 2009, as Manuscript iovs.09-3746, (Sep. 9, 2009), 36 pgs.

Shivdasani, Mohit N., et al., "Evaluation of stimulus parameters and electrode geometry for an effective suprachoroidal retinal prosthesis", J, Neural Eng. 7 (2010) 036008, (May 18, 2010), 11 pgs.

Yanai, Douglas, et al., "Visual Performance Using a Retinal Prosthesis in Three Subjects With Retinitis Pigmentosa", American Journal of Ophthalmology, vol. 143, No. 5, (May 2007), 820-827,e2.

Zrenner, Eberhart, et al., "Subretinal electronic chips allow blind patients to read letters and combine them to words", Proc. R. Soc. B (2010) 00,1-9, doi:10.1098/rspb.2010.1747, (2010), 1-9.

"European Application No. 10836833.3, European Search Report dated Sep. 18, 2014", 11 pgs.

Clements, Mark, et al., "An Implantable Nero-Stimulator Device for a Retinal Prosthesis", 1999 IEEE International Solid-State Circuits Conference, Session 12, Digest of Technical Papers, ISSCC, First Edition (Cat. No. 99CH36278), Jan. 1, 1999, pp. 216-217, 462, 3 pgs.

Everingham, M. R., "Head-mounted mobility aid for low vision using scene classification techniques", The International Journal of Virtual Reality, vol. 3, No. 4, Aug. 31, 1999, pp. 3-12, 3-12.

Frey, Urs, et al., "An 11k-Electrode 126-Channel High-Density Microelectrode Array to Interact with Electrogenic Cells", 2007 IEEE International Solid-State Circuits Conference, Session 8, Biomedical Devices, Digest of Technical Papers, Feb. 1, 2007, pp. 158, 159, 593, 3 pgs.

Palanker, Daniel, et al., "Design of a high-resolution optoelectronic retinal prosthesis", J. neural Eng. 2(1) (Mar. 1, 2005) S105-S120, Institute of Physics Publishing, Bristol, GB, (Mar. 1, 2005), S105-S120.

\* cited by examiner

METHOD AND APPARATUS FOR STIMULATING RETINAL NERVE CELLS

CROSS-REFERENCE TO RELATED APPLICATIONS

The present application is a national stage application under 35 U.S.C. §371 of PCT/AU2010/001637, filed Dec. 2, 2010, and published as WO 2011/072322 A1 on Jun. 23, 2011, which claims priority from Australian Provisional Patent Application No 2009906151 filed on 18 Dec. 2009, which applications and publication are incorporated by reference as if reproduced herein and made a part hereof in their entirety, and the benefit of priority of each of which is claimed herein.

FIELD

The present patent application relates to a method and an apparatus for stimulating retinal nerve cells of a patient to restore or improve vision, particularly through targeted application of electrical current to electrodes in an electrode array of a visual prosthesis.

BACKGROUND

Visual prostheses have been developed to restore or improve vision within blind or partially blind patients. A visual prosthesis commonly includes an implantable component having an electrode array, situated on or in a substrate, for placement in the eye on or near retinal nerve cells. Electrical signals are transmitted via the electrodes to the retinal nerve cells, triggering a perception of light within the patient's brain. The prosthesis can therefore restore or improve vision to patients whose retinal photoreceptors have become dysfunctional.

Commonly, a visual prosthesis is used in conjunction with a video camera. A stream of images detected by the camera is converted into digital signals by an image processor and transmitted in 'real time' to an electrode interface unit. The electrode interface unit is connected to the electrode array via a plurality of conductors and decodes the signals and stimulates the electrodes in accordance with the detected images.

Conventional electrode stimulation techniques apply current to one electrode at a time, and seek to switch between application of current to electrodes of the array fast enough to cause flicker-free vision, either using single or multiple current sources. For epiretinal implants with 16-site electrode arrays it has been shown that fast sequential application of current to electrodes, using a raster scanning process for example, can elicit the perception of continuous elements. Typically, each electrode represents a single "pixel" in a coarse array of pixels derived from the image. Pixel-based techniques such as this are disclosed in US 2008/0058897 A1 and US 2008/0046030 A1, for example.

It is desirable to provide the perception of increased image quality to the patient through use of larger electrode arrays representing images with a greater number and finer spacing of pixels. However, when using larger electrode arrays, including arrays of hundreds or thousands of electrodes, conventional pixel-based techniques have been found to have significant engineering and technical constraints. For instance, when sequential application of current to electrodes is employed in larger arrays, the stimulation may not be fast enough to provide flicker-free vision to the patient.

To solve this problem, simultaneous application of current to multiple electrodes has been performed. However, "crosstalk" or current interactions between the electrodes has been found problematic as it leads to enlarging of the various tissue areas stimulated by the electrodes, blurring stimulation between these areas and thus the resultant image perceived by the patient. In light of this, it has been proposed in US 2006/0241753 A1 to apply current to hexagonal patterns of electrodes using multiple current sources. Hexagonal 'guard' rings of electrodes are created, which each surround a central electrode, and act as current return electrodes, keeping the current applied to the central electrode focussed. By using multiple current sources, current can be applied to many such hexagonal patterns simultaneously. However, this technique requires specialised hardware with multiple current sources, increasing cost and component sizes. The use of hexagonal guard rings also increases thresholds for electrical stimulation and therefore increases the total power consumption of a device when compared to devices having simpler stimulus patterns, such as monopolar stimulus patterns.

Any discussion of documents, acts, materials, devices, articles or the like which has been included in the present specification is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification the term "visual prosthesis" is used to denote apparatus for restoring or improving visual function of a patient, and will be understood to cover devices otherwise known as bionic eyes, artificial eyes, retinal prostheses and retinal stimulators or similar.

SUMMARY

At its most general, the present invention provides methods and apparatuses for stimulating retinal nerve cells using an electrode array, wherein electrical current is applied simultaneously to electrodes of a line of electrodes of the electrode array.

According to a first aspect of the present invention, there is provided a method of electrically stimulating a patient's retina with an electrode array implanted in the patient's eye, the method comprising:

capturing one or more images;

detecting at least one line and/or edge in the one or more images;

identifying a line of electrodes in the electrode array corresponding to a detected line and/or edge; and applying electrical current simultaneously to electrodes of the identified line of electrodes.

According to a second aspect of the present invention, there is provided apparatus comprising:

an electrode array for stimulating a retina;

an image capture device configured to capture one or more images;

an image processor connectable to the image capture device and configured to detect at least one line and/or edge in the one or more captured images; and an electrode interface connectable to the processor and adapted to apply electrical current simultaneously to electrodes of a line of electrodes in the electrode array corresponding to a detected line or edge.

According to a third aspect of the present invention, there is provided an implantable component comprising:
an electrode array; and
an electrode interface connectable to an image processor, the image processor configured to detect at least one line and/or edge in one or more captured images, the electrode interface being adapted to apply electrical current simultaneously to electrodes of a line of electrodes in the electrode array corresponding to a detected line or edge.

The human visual system has been found to be particularly sensitive to lines or edges, which are crucial to distinguishing shapes and relative locations of objects. The human visual system is primarily concerned with providing humans with awareness of their surroundings, particularly to allow mobility. Accordingly, by providing the perception of lines or edges to the patient, in preference to pixelated images, for example, a particularly efficient and effective way of achieving a functional level of vision through electrical stimulation with an electrode array can be realised.

It has been found by the present inventors that applying electrical current to electrodes of a line of electrodes simultaneously provides significant benefits over applying current to single electrodes in a sequential fashion. For example, stimulation can be much faster, because current is applied to electrodes of the line at once, and because targeting lines and edges means current may need to be applied to fewer electrodes, in comparison to techniques where current is applied to all electrodes of an array sequentially, for example.

In the aspects of the invention, preferably a single current source is used, the electrode interface applying current from the single current source simultaneously to the electrodes. The electrode interface may be capable of coupling any combination of electrodes to the single current source in parallel.

Significant power saving may be achieved using a single current source, in comparison to sequential 'raster'-type stimulation of electrodes, or techniques using multiple current sources, as identified for conventional stimulation techniques. Particularly, by taking an approach in accordance with the present invention, it has been found that the threshold charge $q_t(\mu C)$ per pulse applied simultaneously to electrodes in a line of electrodes, in order to evoke a response in the visual cortex, is not directly proportional to the number of electrodes to which the charge is applied simultaneously. Most notably, the total threshold charge per pulse $q_t(\mu C)$ has been found to be much lower than the total threshold charge per pulse one would expect, and which is encountered in conventional techniques, calculated by simply summing the threshold charge per pulse for each of the electrodes $q_i(\mu C)$ when the charge is applied separately (i.e., non-simultaneously). Accordingly, in the present invention, to take advantage of the observed phenomenon, the total charge per pulse that is applied simultaneously to the electrodes of each line of electrodes $q_t(\mu A)$ can be less than $\Sigma q_i(\mu C)$, i.e.:

$$q_t(\mu C) < \Sigma q_i(\mu C)$$

The reduction in the total threshold charge per pulse, is accompanied by a lower resistance or impedance for a line of electrodes when current is applied to the electrodes simultaneously, in comparison to sequentially. The reduction in impedance means lower power and lower voltage are required when applying current to electrodes of a line of electrodes simultaneously.

By reducing power consumption and/or the number of current sources required, a smaller power source and electrode interface may be useable, and smaller electronic componentry may be employed, reducing the size of the prosthesis.

Further reduction in power may be achieved using larger electrodes (i.e., electrodes with larger tissue contact/stimulation areas) and wider pulses. In this regard it has been found that, when constant current electrical pulses with wide pulse width, e.g., >500 µs per phase, are applied simultaneously to electrodes of a long line of electrodes (e.g., 12 electrodes), the total threshold current for a line of relatively large electrodes is similar to the total threshold current for a line of relatively small electrodes. Since the impedances of larger electrodes are lower than those of smaller electrodes, the size of the voltage needed for larger electrodes is lower than for smaller electrodes, and thus total power consumption when using larger electrodes can be reduced.

Furthermore, it is apparent that the threshold current tends to plateau for larger electrodes, meaning that total threshold currents can be, relatively, much lower when longer lines of larger electrodes are used. In one embodiment of the present invention, "large" electrodes may have diameters greater than 160 µm, or diameters greater than 200 µm, or diameters greater than 250 µm, or diameters greater than 300 µm. The diameters may be less than 800 µm.

Still furthermore, it has been found that, by taking an approach in accordance with the present invention, where electrical current is applied to electrodes of a line of electrodes simultaneously, a cortical response may be achieved in the patient in relation to stimulation positions of the retina where a response may not otherwise be achievable through single electrode stimulation. The stimulation positions may correspond to the periphery of the retina, for example, giving the patient a wider perceived field of view. Also, when electrical current is applied to electrodes of a line of electrodes simultaneously, a more localised activation of the visual cortex has been observed. This means that relatively sharp lines may be perceived by the patient, in comparison to an approach in which current is applied sequentially to electrodes of a line of electrodes, for example, where a smearing or spreading of the lines may be perceived.

Although cross-talk has been found problematic in pixel-based techniques where current is applied to multiple electrodes simultaneously, in approaches according to the above aspects, where the stimulation of lines of electrodes is targeted, cross-talk has been found advantageous. Particularly, it has been found that cross-talk between adjacent electrodes will tend to enhance, rather than reduce, the quality of the retinal stimulation. This is because the spreading of the retinal stimulation between adjacent electrodes may provide, in effect, a more continuous line of stimulation. Thus, the lines or edges perceived by the patient may be stronger.

In light of the advantages highlighted above, it is conceived that, in the methods and apparatuses of the present invention, the application of current simultaneously to electrodes of lines of electrodes in the electrode array may be performed exclusively. Thus, there may be no application of current at all to single electrodes independently of other electrodes (i.e. non-simultaneously), and there may be no application of current at all to combinations of electrodes that are not in a line. Nonetheless, it is conceived that in some embodiments, in addition to applying current simultaneously to electrodes of lines of electrodes, current may be applied non-simultaneously to single electrodes, or applied simultaneously to combinations of electrodes, forming contiguous collections of electrodes, for example, that are not in a line.

In one embodiment, application of current to electrodes of lines of electrodes may be carried out on electrodes present in one or more regions of the electrode array only, the regions positioned to stimulate one or more regions of the retina only.

A first region of the electrode array for stimulating a first region of the retina, and a second region of the electrode array for stimulating a second region of the retina, may be determined. Current may be applied simultaneously to electrodes of one or more lines of electrodes located in the second region of the electrode array and, additionally, current may be applied non-simultaneously to one or more single electrodes located in the first region of the electrode array. The second region of the retina may be located radially outwards of the first region of the retina, for example. Thus, the second region of the retina may be a peripheral region of the retina, and the first region of the retina may be a central region of the retina, for example.

The locations of the first and second regions of the electrode array may be determined based on the response of the patient to (i) the application of electrical current non-simultaneously to one or more single electrodes at different locations of the electrode array, and/or (ii) the application of electrical current simultaneously to electrodes of one or more lines of electrodes at different locations of the electrode array.

For example, current may be applied to single electrodes, or multiple electrodes non-simultaneously, that are positioned in an implanted electrode array to stimulate cells at or near a central region of the retina, where a relatively low threshold to invoke a visual percept in the patient may be required, whereas current may be applied simultaneously to electrodes of lines of electrodes that are positioned in the implanted electrode array to stimulate cells at or near the periphery of the retina, where invoking a visual percept in the patient might otherwise be very difficult or impossible with single electrode stimulation.

The different stimulation strategies may be performed exclusively in the respective regions. Alternatively, non-exclusive use of these stimulation strategies in one or more of the regions may be employed.

The shape and orientation of a line of electrodes, and its length, may be dependent on the nature of the detected line or edge to which it corresponds. For example, depending on the detected line or edge, the line of electrodes may be a straight line of electrodes or a bent or curved line of electrodes. The line of electrodes may be a row or column of electrodes within a grid pattern. The line of electrodes may be a diagonal line of electrodes within a grid pattern. The line of electrodes may be a curved or bent line of electrodes that winds across several rows or columns of a grid pattern. The electrodes of the electrode array may be distributed in a square grid pattern (electrodes of adjacent rows and columns being aligned with each other), or a hexagonal grid pattern (electrodes of adjacent rows and columns being offset from each other), or a less regular distribution of electrodes may be employed. The line of electrodes may extend in a loop. For example, the line may be comprised of electrodes at the outer edge of a contiguous collection of electrodes (i.e., an outline of a collection), simultaneous application of current being excluded from the interior electrodes. Such a line of electrodes may by used to represent an edge of a shape. Although a better representation of the shape may be achieved by applying current simultaneously to electrodes of the entire outline, it is conceivable that current may be applied to segments of the outline sequentially or otherwise.

The electrodes of a line of electrodes may be all the electrodes along the line. Alternatively, the electrodes of a line of electrodes may be a selection of electrodes along the line. For example, current may be applied to every second electrode, 2 in every 3 electrodes, or a less regular selection of electrodes. A line of electrodes according to the present invention may have a minimum number of electrodes that is greater than 2 electrodes. For example, current may be applied to electrodes of lines of electrodes comprising at least 3 electrodes, at least 5 electrodes or at least 10 electrodes. The minimum number of electrodes in a line may, however, depend on the total number of electrodes in the electrode array.

A bipolar or monopolar technique to the stimulation of retinal nerve cells may be employed. In a bipolar technique, one or more electrodes of the electrode array may act as a current return electrode for current applied to the line of electrodes. The current return electrode may be located at a relatively remote part of the array from the line of electrodes, separated from the line of electrodes by one or more inactive electrodes. In a monopolar technique, the current return path may be via an electrode remote from the eye or remote from the electrode array on the retina. In this case current applied to the line of electrodes is dispersed within the patient's eye and does not cause stimulation of retinal cells other than those close to the line of stimulating electrodes within the electrode array.

Although current is applied simultaneously to electrodes of each line of electrodes, current may nevertheless be applied to different lines of electrodes sequentially. Thus, after current is applied simultaneously to electrodes of one line of electrodes, subsequently current may be applied simultaneously to electrodes of another line of electrodes. In some embodiments, this technique may be employed alongside a pixel-based stimulation technique, i.e., a technique in which sequential application of current to individual electrodes is carried out. Thus, in some embodiments, application of current simultaneously to electrodes of each line of electrodes may be carried out exclusively, and in other embodiments, there may be additional approaches taken to the application of current to electrodes.

The image capture device, e.g., a camera, may be connected via wires, or wirelessly, to the image processor apparatus. Likewise, the image processor may be connected to the electrode interface via wires, or wirelessly. The electrode interface is preferably capable of directing current from a single current source to any combination of electrodes in the electrode array simultaneously (e.g., by connecting to the electrodes in parallel). The electrode interface may comprise a cross-point switch matrix or a bank of switches, etc. Electrical current may be supplied to the electrode interface from a constant voltage or constant current stimulator, which may be capable of adjusting easily the output voltage or current supply to compensate for different impedances at the electrode-tissue contact region and provide the required charge per pulse for application to the electrodes simultaneously.

The electrode array of the present invention may be implanted in a number of different positions in the eye, such as epiretinally (overlaying the retina), subretinally (between the retina and the choroid), suprachoroidally (between the sclera and the choroid layers of the eye) or episclerally (directly on the sclera). The methods and apparatuses described herein may be used in conjunction with an electrode array implanted in a position in the eye that would not normally be considered appropriate using standard techniques. Suprachoroidal implantation of an array may provide reduced surgical risks to the patient in comparison to subretinal implantation, but, since a suprachoroidally implanted array will be located further away from target cells than a subretinally implanted array, suprachoroidal implantation has often been considered inappropriate due to the high threshold currents and charges required to achieve stimulation. Using the methods and apparatuses described herein with respect to a suprachoroidally implanted electrode array may overcome these problems by lowering threshold current and charges.

The image processor may be calibrated prior to and/or after fitting the electrode array in the patient's eye. Calibration may involve measurement of thresholds, growth of brightness as a function of charge per pulse, and/or a spatial mapping procedure, etc.

Each line of electrodes identified as corresponding to a detected line and/or edge in the one or more captured images may correspond to the detected line and/or edge to the extent that the line of electrodes is intended to stimulate visual perception by the patient of substantially an identical or similar line and/or edge to the detected line and/or edge, to the closest extent possible. However, in identifying the line of electrodes, other factors may be taken into account, such as one or more parameters calculated during the calibration of the electrode array, meaning that the identification of the line of electrodes corresponding to the detected line and/or edge may be a balance between providing the visual perception to the patient of substantially an identical or similar line and/or edge to the detected line and/or edge, to the closest extent possible, and choosing electrodes a line of electrodes that have desired charge or current thresholds or impedance values, etc., to achieve reductions in power consumption of the apparatus, for example.

To help identify a line of electrodes corresponding to a detected line and/or edge, regions of the image capture area may be mapped to different electrodes of the electrode array. As an example, where the image capture device (e.g. a digital video camera) comprises a pixelated detector, e.g., a charge coupled device (CCD) optical detector, pixels of the CCD device may be mapped directly to electrodes of the electrode array.

Nonetheless, the spatial mapping may take into account the position of the electrode array relative to the retina and/or regions of the retina, i.e. take into account an anatomical and/or spatial alignment factor. Certain regions of the retina may be affected by disease conditions, rendering some retinal cells dysfunctional, for example. In view of these considerations, the position of the array, after and/or during insertion within the eye, may be determined and the spatial mapping may be adjusted accordingly. The position may be determined with respect to anatomical landmarks such as the optic disk and vascular arcades. Since the position of the electrode array in the eye strongly dictates the spatial mapping of stimulation to the nerve cells, and the patient's brain, the spatial mapping may ensure that current is applied only to electrodes that are appropriately positioned to stimulate nerve cells and/or to stimulate nerve cells in a manner ensuring lines and edges perceived by the patient are suitably positioned in the patient's perceived field of view. In a rudimentary example, if the array is oriented more to left of the optical disk than intended, the spatial mapping onto the electrode array may be biased toward the right side of the electrode array to compensate. Since there may be some settling of the position of the electrode array after insertion into the eye over a number of weeks, the spatial mapping may be repeated, as part of a recalibration procedure, a reasonable period after insertion, or the spatial mapping may be deferred entirely until a reasonable period after insertion.

The initial mapping procedure may take into account not only the anatomical positioning of the array relative to the retina as discussed above, but additionally or alternatively, the electrophysiological response of the retina, optic nerve, visual cortex or other part(s) of the visual pathway to electrical pulses delivered from the electrodes. For example, the electrophysiological evoked potential response of the patient, to stimulation by electrodes at different positions relative to the retina, may be determined, to understand whether certain electrodes are appropriate for use and/or to determine the type of stimulation different electrodes give the patient. Furthermore, monitoring the electrophysiological evoked potential response may be used to determine threshold levels of electrical current/charge per electrical pulse required to achieve different levels of stimulation of the retinal nerve cells. The levels may be dependent on the positioning of the electrodes relative to the retina. For example, it has been found that electrodes in the array adjacent to a central section of the retina may have lower threshold levels than electrodes located toward the periphery of the retina. More marked variations in thresholds may therefore be seen for arrays providing a wider field of view for the patient.

During calibration of the image processor, electrophysiological evoked potential response monitoring, or a number of other more conventional electrical test procedures, may be used to determine whether any electrodes have faults, such as being short-circuited, inoperative and/or defective.

The image processor may employ line and/or edge extraction techniques to detect the existence of lines and/or edges in the images, and to determine the position, length, shape, and/or orientation of the detected lines and edges. The intensity of lines, e.g., their brightness and/or contrast relative to the surrounding image areas, may also be determined. Furthermore, the intensity of edges, e.g. the changes in the brightness or contrast at the boundary between adjacent elements of the images, which changes typically define edges, may be determined.

The image processor may include means for ranking the lines and edges in terms of their importance. Ranking can be based on any one or more of the line or edge characteristics determined during the extraction procedure, such as intensity and/or length. A brighter line, or a longer line, may be ranked higher than a dimmer line or shorter line, for example. Thus, the ranking may be carried out to order the lines and edges in terms of their visual importance to a patient, ensuring that the most conspicuous lines and edges of an image are presented first to the patient, or indeed are presented at all.

More advanced ranking procedures may employ image recognition techniques. For instance, the image processor may detect a shape in an image (e.g., a doorway) and recognising that the position and/or length of certain lines or edges of the shape are of particular relevance to the patient (e.g., the inner edges of a doorway), rank the corresponding lines or edges higher than others. This type of ranking may be in addition to, or regardless of, determination of other parameters such as the intensity or length of the lines or edges.

A charge mapping procedure may be carried out by the image processor, or an additional processor connected to the image processor, for each line and edge detected and/or for each line or edge meeting a predetermined ranking threshold. Taking into account information gathered during the calibration procedure or otherwise, the charge mapping procedure may identify which line of electrodes of the electrode array should be used to stimulate the retinal nerve cells, dependent on the length, shape, position and/or orientation of a detected line or edge. The charge mapping procedure may also determine the appropriate charge per pulse to be applied simultaneously to the electrodes of a line of electrodes, and optionally to other electrodes simultaneously or non-simultaneously, dependent on e.g., the intensity of the detected line or edge and the characteristics of the electrodes (e.g., as determined during the calibration procedure). The charge mapping procedure may also determine the appropriate pulse width of the current signal used for stimulating the line of electrodes. The charge per pulse may be adjusted by either adjusting the current or pulse width or both. The choice of pulse width may be a balance between a desire to reduce voltage and power consumption (it has been determined that using longer pulses means, generally, that less current and therefore less voltage, but higher charge, is required to achieve threshold stimulation) and a desire to increase the speed of stimulation (using shorter pulses permits quicker sequential application of current to lines of electrodes as well as lower charge to achieve stimulation).

Having performed the charge mapping procedure, a digital signal encoded with corresponding data can be sent from the processor to the electrode interface, via wires, or wirelessly, and the electrode interface can decode the signal and apply current simultaneously to the electrodes of a line of electrodes in accordance with the data and optionally to other electrodes simultaneously or non-simultaneously.

A serial based approach may be taken to the charge mapping procedure. The lines and edges may be processed in a FIFO (first in first out) basis. Accordingly, after ranking of lines and edges, the charge mapping can be carried out for one line or edge, and the appropriate signal sent to the electrode interface, prior to charge mapping of the next line or edge. Nonetheless, it is conceived that simultaneous processing of lines and edges might be carried out.

As discussed, by applying electrical current simultaneously to electrodes of a line of electrodes, a visual percept may be achieved in relation to a particular region of the retina that may not otherwise be achievable through application of current non-simultaneously to one or more single electrodes, for example. Although this technique may be used in combination with the methods and apparatuses discussed in relation to the preceding aspects, it may also be used in combination with other methods and apparatuses. For example, it may be used in conjunction with a method or apparatus in which a line or edge in one or more captured images is not necessarily determined.

Thus, according to a fourth aspect of the present invention there is provided a method of electrically stimulating a patient's retina with an electrode array implanted in the patient's eye, the method comprising:

determining a first region of the electrode array for stimulating a first region of the retina and a second region of the electrode array for stimulating a second region of the retina, applying electrical current non-simultaneously to one or more single electrodes located in the first region of the electrode array; and applying electrical current simultaneously to electrodes of a lines of electrodes located in the second region of the electrode array.

Furthermore, according to a fifth aspect of the present invention there is provided apparatus comprising:

an electrode array for stimulating a retina of a patient, the electrode array comprising a first region for stimulating a first region of the retina and a second region for stimulating a second region of the retina; and an electrode interface adapted to apply electrical current simultaneously to electrodes of a line of electrodes located in the second region of the electrode array; and adapted to apply electrical current non-simultaneously to one or more single electrodes located in the first region of the electrode array.

Any one or more features described with respect to the first, second and third aspects of the present invention may be combined with the method or the apparatus according to the fourth or fifth aspects of the invention.

BRIEF DESCRIPTION OF THE DRAWINGS

By way of example only, embodiments are now described with reference to the accompanying drawings, in which.

DETAILED DESCRIPTION

Figure 1:
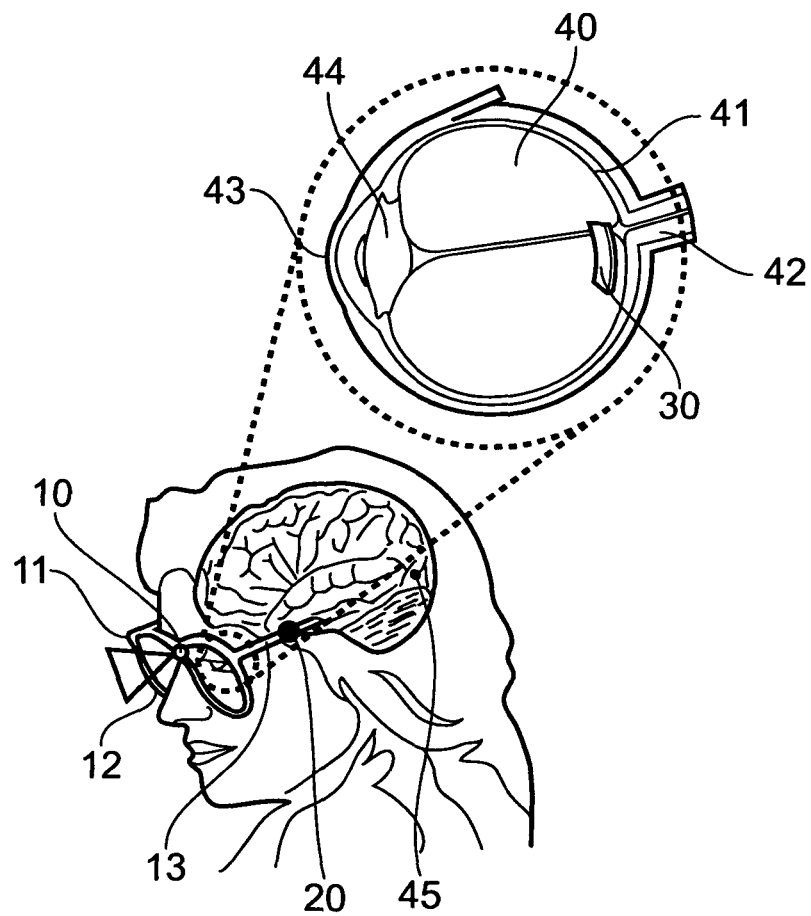
FIG. 1 shows visual prosthesis apparatus for applying current to an implantable electrode array in accordance with an embodiment of the present invention.

Referring to FIG. 1, apparatus according to one embodiment, for stimulating an electrode array implanted in a patient's eye, is provided. The apparatus comprises a video camera 10, located on lens frames 11 of a pair of glasses 12, for capturing a sequence of images. The camera 10 is connected via a cable to an image processor 20, located on one arm 13 of the glasses. The processor 20 is arranged to process the captured images and deliver, via a transmitter, a digital data stream to an implantable visual prosthesis component 30 located e.g., suprachoroidally in a patient's eye 40, i.e., between the sclera and choroid layers of the eye, adjacent the retina 41 and disc of the optic nerve 42, at the back of the eye opposite the cornea 43 and lens 44. The implantable component 30 is arranged to stimulate retinal nerve cells in response to the data stream, causing nerve impulses in the visual centre 45 to be activated, eliciting the perception of vision by the patient.

Figure 2:
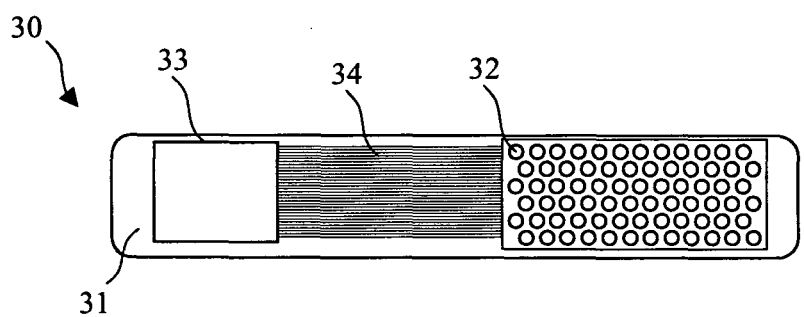
FIG. 2 shows a schematic plan view of an embodiment of an implantable component that may be used in the apparatus of FIG. 1.

With reference to FIG. 2, the implantable component 30 in one embodiment comprises a substrate 31, an array of electrodes 32, an electrode interface unit, particularly a cross point switch matrix 33, and a plurality of conductors 34, each conductor 34 connecting a respective one of the electrodes of the electrode array 32 to the switch matrix 33. The switch matrix 33 is connected to a single current source 35 (constant current stimulator), preferably located beneath the skin externally to the eye, and is capable of applying electrical current to any combination of the electrodes in parallel. Although the current source 35 is not located in the implantable component 30 in this embodiment, in alternative embodiments, the current source may be included in the implantable component, in addition to the switch matrix, and the current source may be located close to the electrode array, for example. The switch matrix is controlled using the image processor 20, which runs modular software and controls the switch matrix in response to the digital data stream.

Figure 3:
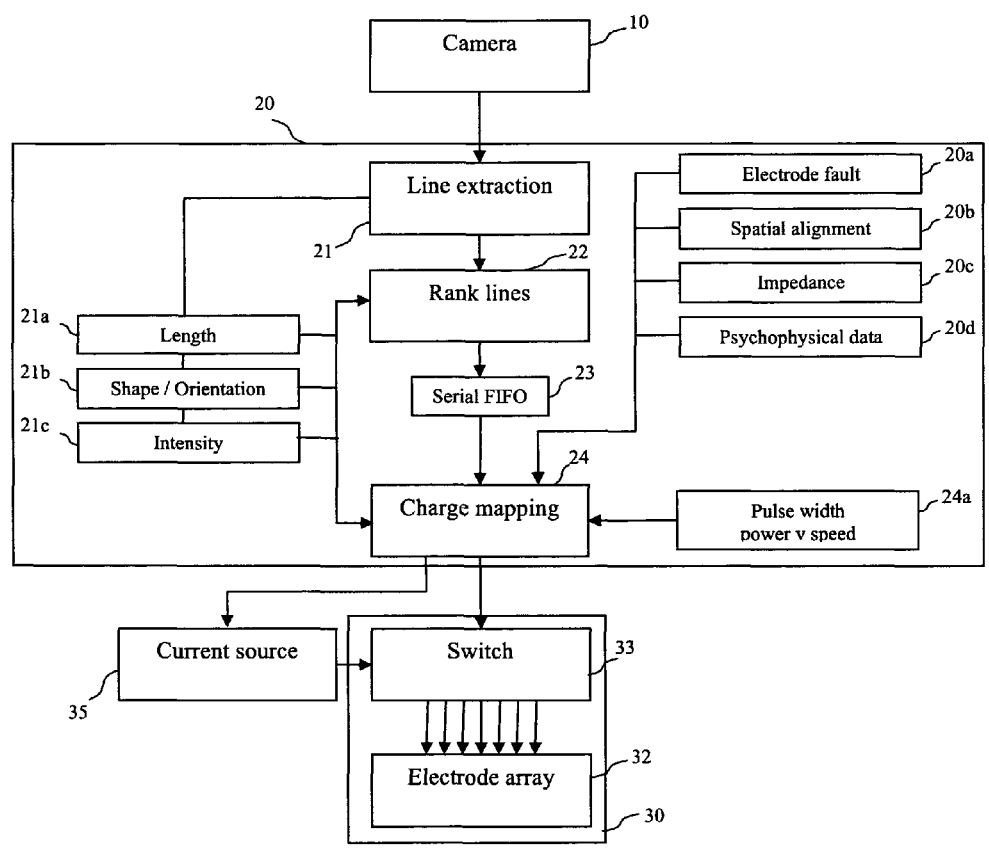
FIG. 3 shows a flow chart detailing processing steps employed in a method of stimulating retinal nerve cells, which may be used in the apparatus of FIG. 1.

The functionality and possible method of use of the apparatus of this embodiment is now described in more detail with reference to the flowchart of FIG. 3.

Prior to and after insertion of the implantable component 30 into the eye, a calibration procedure is employed, with information gathered during the calibration procedure imparted to the image processor 20 and stored for use in a subsequent charge mapping step 24. In the calibration procedure, electrode fault testing 20a is carried out to determine whether any electrodes are short-circuited, inoperative and/or defective etc. Furthermore, an anatomical/spatial alignment step 20b is carried out, in which the alignment of the electrode array 32 relative to the retina (or other anatomical landmark in the eye) is determined. Furthermore, an impedance measuring step is carried out 20c. Still furthermore, threshold psychophysical testing step 20d is carried out, to determine the levels of current/charge per pulse that must be applied to the electrodes to achieve adequate visual responses, the dynamic range of stimulation between threshold and maximum brightness, and the perceived position of the phosphenes evoked by stimulation of each electrode and/or each line of electrodes in the patient.

During use of the apparatus to stimulate the patient's retinal nerve cells, digital images captured by the camera 10 are sent sequentially to the image processor 20, which, controlled by appropriate software, performs a sequence of processing steps. Initially, the processor 20 carries out a line and edge extraction step 21 for the first captured image, analysing the captured image to find lines and edges in the image, and detecting and storing parameters such as the length 21a, shape and orientation 21b and intensity 21c of any detected lines and edges in the image, using feature extraction techniques. Next, a ranking step 22 is carried out, to rank the detected lines and edges in accordance with their importance (e.g., in terms of their prominence in the image and/or relevance to the patient), based on detected and stored parameters such as their length 21a, shape/orientation 21b and intensity 21c. Subsequently, lines and edges meeting a predetermined ranking threshold are subject to, in a first in first out basis 23, a charge mapping procedure 24. In the charge mapping procedure 24, the image processor identifies which electrodes, forming a line of electrodes, of the electrode array should receive current simultaneously for each line or edge being processed. The charge mapping 24 takes into account information acquired during the calibration procedure such as any electrode faults 20a, the electrode array positioning/spatial alignment 20b, the electrode impedance values 20c and psychophysical data 20d. The selected line of electrodes is scaled according to the length 21a of the detected line or edge, and arranged in accordance with the shape and orientation 21b of the detected line or edge. An appropriate charge to be applied simultaneously to the electrodes is determined based on the intensity 21c of the line or edge, the electrode impedance values 20c and psychophysical data 20d, and the pulse width 24a of the current signal. The pulse width 24a is ideally chosen to be small enough to achieve a stimulation speed that avoids the perception of flickering in the images perceived by the patient, yet optimised to keep voltage at an appropriately low level. Although a constant current stimulator is used to supply power in this embodiment, in alternative embodiments, a constant voltage stimulator may be used. To achieve the required charge per pulse, if the voltage is increased, the electrical signal may have a narrower pulse width and vice-versa. Thus, there will be a similar trade off between voltage and speed associated with a voltage based stimulator.

Following the charge mapping procedure 24 for a line or edge, the image processor is configured to send encoded information to the cross-point switch matrix 33 of the implantable component 30 and to the current source 35. The encoded information identifies the electrodes to which current is to be applied simultaneously, in addition to the current level and pulse width to be applied by the current source 35. The switch matrix 33 is arranged to decode the signal to ascertain this information and route electrical current from the single current source 35 simultaneously to electrodes of a line of electrodes in the electrode array 32, in accordance with the decoded information, whereupon the line of electrodes stimulates the retinal nerve cells. After or during this stimulation step, the next ranked line or edge is subject to the charge mapping procedure 24 set out above, and so forth until the final line or edge, meeting the predetermined ranking threshold, in a single image, has been processed and 'delivered' to the patient. The whole process can be repeated for each image captured by the camera 10, or a selection of images captured by the camera (e.g. every second image captured or otherwise), to provide continuous visual perception to the patient.

Example 1

A flexible visual prosthesis having a 6×12 array of electrodes was implanted in the suprachoroidal space, between the sclera and the choroid, of normally sighted adult cats. The spacing between adjacent rows was 0.8 mm and the spacing between electrodes on each row was 1 mm. Electrodes of different sizes were used on different rows of the array, including electrodes of 395 µm diameter on one row and electrodes of 160 µm diameter on other rows. The electrode arrays were connected to a single current source via a cross-point switch matrix, enabling electrical current to be applied to any combination of the electrodes simultaneously.

Figure 4B:
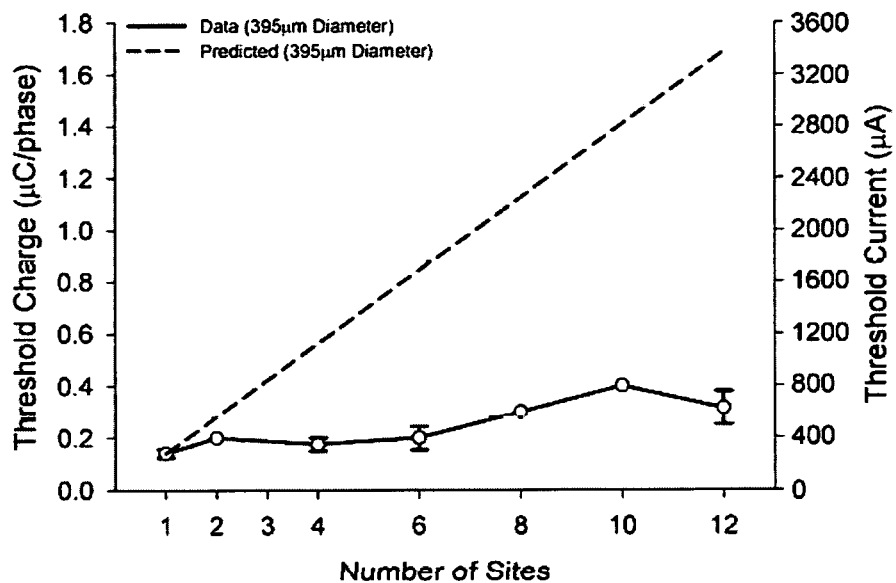
FIGS. 4A and 4B show graphs of exemplary mean current and charge thresholds as a function of the number of electrodes of a row of electrodes that current is applied to simultaneously, and predicted thresholds extrapolated from the thresholds for a single electrode.
Figure 4A:
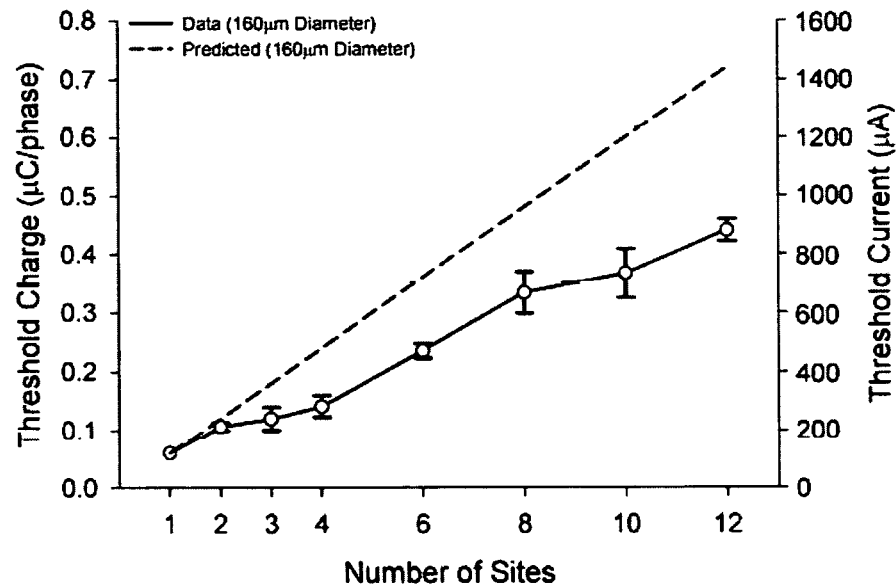
Figure 5:
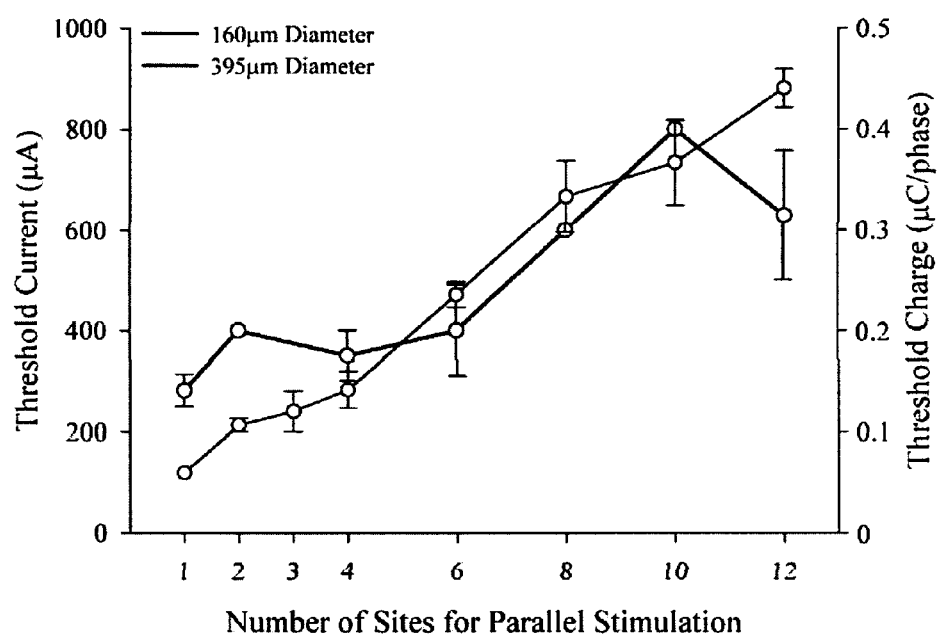
FIG. 5 shows a graph of the mean current and charge thresholds from FIGS. 4A and 4B superimposed.
Figure 6:
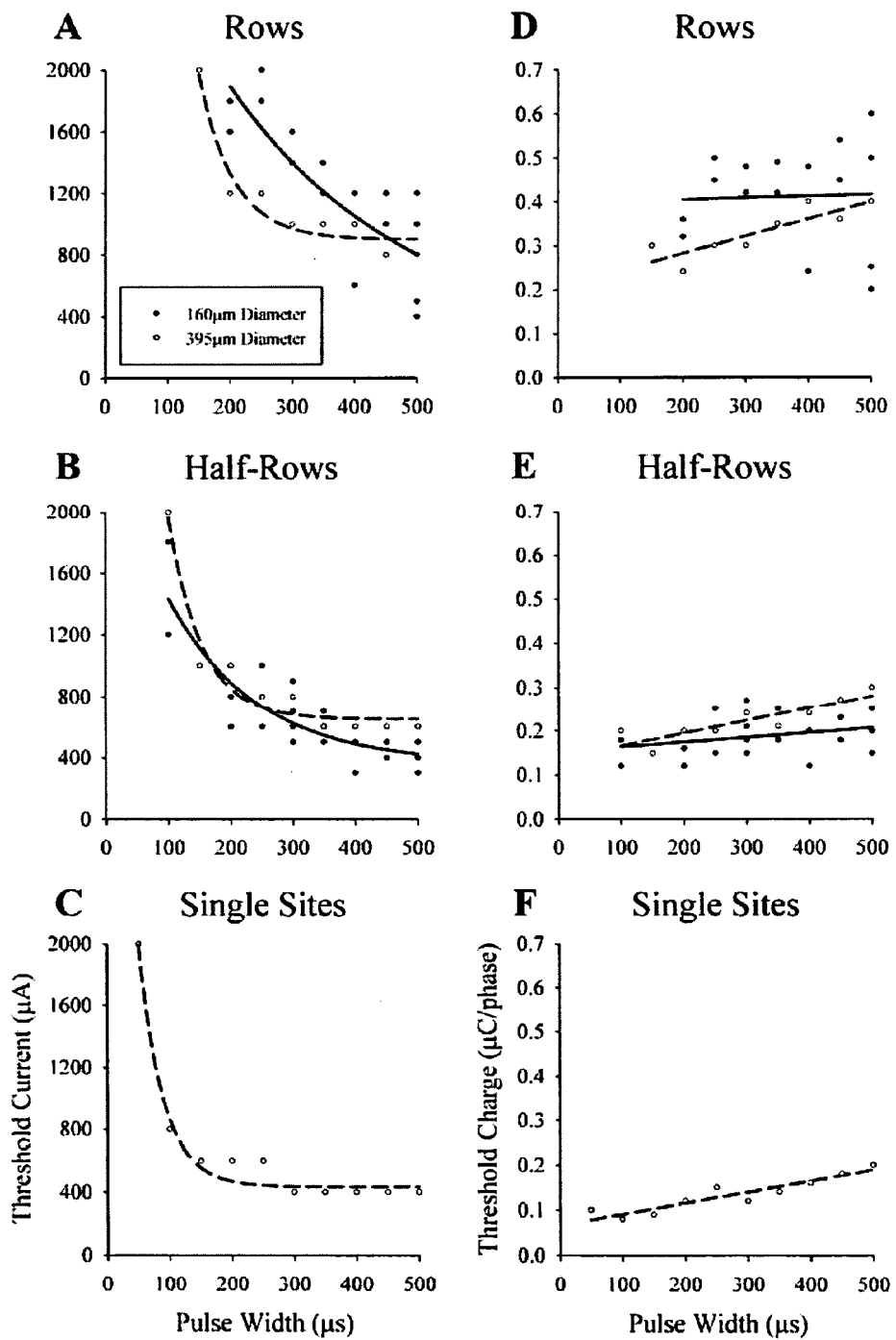
FIGS. 6A to 6C, and FIGS. 6D to 6F, show graphs of exemplary total threshold current and threshold charge respectively, as a function of pulse width, for lines of electrodes with differing lengths within a row of electrodes, and for single electrodes.

The threshold current and threshold charge per pulse for a number of different lines of electrodes, was measured and the results plotted graphically (see FIGS. 4A, 4B and 5). In this example, the threshold current and threshold charge per pulse were defined as the values that yielded positive-going peaks, within 30 ms from stimulus onset, of at least 0.3 mV of electrically evoked cortical potential. On the whole, these values were substantially indicative of a minimum current, and minimum charge per pulse, to be delivered to lines of electrodes in order to evoke a response in the visual cortex.

It was found that there was substantially no difference in the amount of charge required to reach threshold stimulation of the 160 µm diameter electrodes compared to the 395 µm diameter electrodes, although the charge density for the 395 µm electrodes was much lower. It was observed that the threshold charge per pulse tended to increase when current was applied simultaneously to increasing numbers of electrode on a row. However, for both electrode diameters, the threshold currents and charges were found to be considerably lower than the total threshold currents and charges that would have been expected had each electrode of the line of electrodes under test been delivered current separately (e.g., sequentially).

With reference to FIG. 4A, for electrodes with 160 μm diameter, the increase in the threshold current and charge upon increasing the number of electrodes receiving current simultaneously in the line was substantially linear. However, the rate of increase was about half what could have been predicted based on an extrapolation from the threshold currents and charges required for a single electrode that is delivered current separately, as indicated by the broken line in FIG. 4A.

With reference to FIG. 4B, for electrodes with 395 μm diameter, although there was a general trend toward an increase in the threshold current and charge upon increasing the number of electrodes in the line, the rate of increase was almost negligible in comparison to predicted levels based on an extrapolation from the threshold currents and charges required for a single electrode delivered current separately, as indicated by the broken line in FIG. 4A. The threshold current and charge for lines of two or more electrodes was found to be about one-sixth of the thresholds values predicted.

One can infer from FIGS. 4A, 4B and 5, that, through application of current simultaneously to electrodes of lines of electrodes (e.g., to 12 electrodes in a line), a charge/current reduction of 2-6 fold may be achieved, dependent on the electrode diameter. This reduction, along with the reduced impedances, may result in several-fold reduction in power, in comparison to pixel-based techniques.

With reference to FIGS. 6A to 6F, the effect of increasing the pulse widths of the signals used for electrical stimulation of the electrodes, up to a pulse width of about 500 μs, was tested for lines of 160 μm and 395 μm diameter electrodes. It was observed that, within this range, the threshold current for stimulation of entire rows (lines of 12 electrodes), half rows (lines of 6 electrodes) and single electrodes, reduced exponentially with increasing pulse widths. When converted to charge, threshold charge levels for the larger, 395 μm, diameter electrodes tended to increase linearly with increasing pulse widths, whereas threshold charge levels for smaller, 160 μm, electrodes did not exhibit any substantial change.

The results, as shown in FIGS. 4A to 6F, for example, were indicative of the substantial power reduction that can be achieved by applying current simultaneously to electrodes of a line of electrodes in an electrode array, in comparison to sequential application of current to the electrodes. Particularly, the threshold current and charge required to elicit neural activity at the level of the primary visual cortex by applying current to multiple electrode sites in a line simultaneously, using a single current source and a suprachoroidally placed implant in this instance, was much less than that expected from extrapolating the power required for eliciting neural activity through application of current to a single electrode. This technique of simultaneous application of current, coupled with a suprachoroidal electrode array design with large diameter electrodes, and use of wide pulse widths, provides power-efficient stimulation of line-based patterns. The benefit of large diameter electrodes is the lowering of impedances, and tuning pulse widths means lower voltages may be required to reach desired thresholds, which can significantly lower power consumption, and voltage compliance requirements for the stimulator.

Example 2

A platinum electrode array was implanted into the suprachoroidal space in 4 anesthetized adult cats. The array comprised 84 electrodes, arranged in a 7 row×12 column configuration. Adjacent rows were approximately 0.8 mm apart and adjacent the columns were approximately 1 mm apart, and the diameter of each electrode was approximately 400 μm. The cortical response of each animal to monopolar stimulation, through the application of biphasic current pulses with 500 μs pulse width to electrodes of the arrays, was monitored and recorded. Three modes of stimulation were evaluated: (i) application of current to a single electrode on its own; (ii) application of current simultaneously to all 6 electrodes of a half row of electrodes; and (iii) application of current simultaneously to all 7 electrodes of a column of electrodes.

Figure 7:
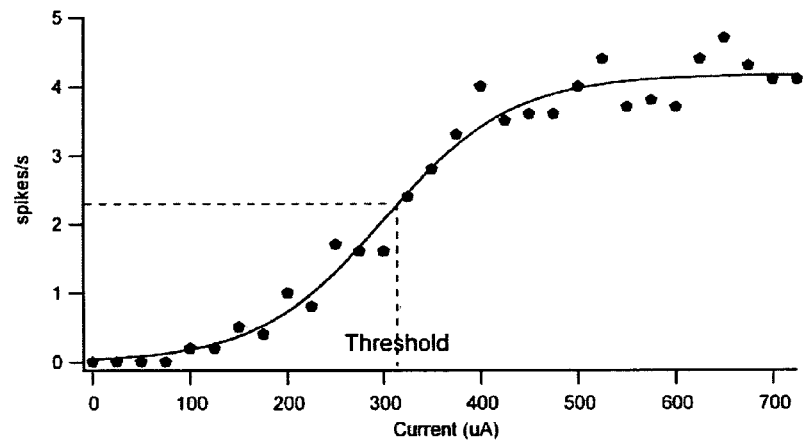
FIG. 7 shows a plot of exemplary spike rate versus current applied to electrodes, for a cortical channel.

Threshold currents and charges to elicit stimulation of the cortex were calculated for each mode of stimulation. In this example, thresholds for each mode of stimulation were determined by plotting the spike rate (calculated in the time window 3-20 ms from stimulus onset) versus current applied to the electrodes, for each recorded channel in the cortex (see FIG. 7 as an example). The threshold was defined as the current required to elicit half the maximum spike rate on that cortical channel, as represented by the dotted lines in FIG. 7.

Figure 8A:
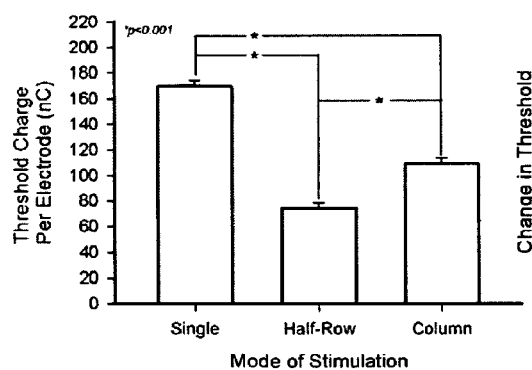
FIG. 8a shows a graph of exemplary mean threshold charges per electrode for a best single electrode, half-row of electrodes and column of electrodes, for multiple cortical channels.

For each cortical channel, the single electrode, half row of electrodes, and column of electrodes, of the implanted electrode array, that had the lowest current/charge threshold for cortical stimulation, when stimulated in accordance with the respective mode of stimulation, was determined and recorded (referred to hereinafter as the "best" single electrode, half row of electrodes, and column of electrodes). FIG. 8a shows a plot of the mean threshold charge per electrode for all the best single electrodes, half-rows of electrodes and columns of electrodes, for all cortical channels recorded. The results indicate that the best half-rows and best columns elicit cortical activity with significantly lower ($p<0.001$) thresholds per electrode compared to the best single electrode. This is generally consistent with the results discussed above with respect to Example 1. However, it is notable that the threshold charge per electrode for the best half-row of electrodes is significantly lower ($p<0.001$) compared to the best columns of electrodes, despite the half-row comprising one less stimulated electrode than the column. It is considered that this may be due to cortical responses being affected by the different (substantially perpendicular) orientation of the rows and columns of electrodes, relative to the retina or the different spacing of electrodes along the rows and columns of the electrode array.

Figures 9A, 9B, 9C:
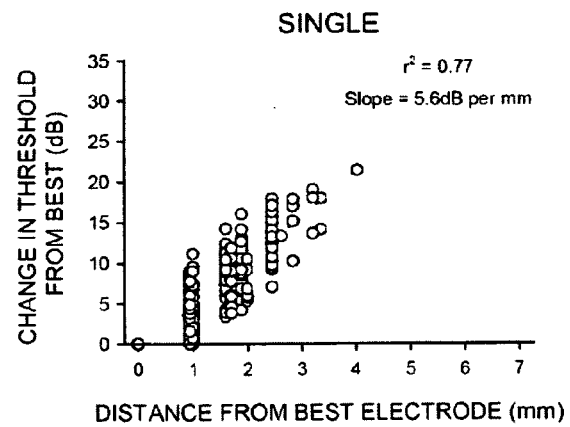
FIGS. 9a to 9c show plots of the exemplary changes in threshold (dB) for single electrodes, half-rows of electrodes and columns of electrodes, as a function of distance (mm) from a best single electrode, half-row of electrodes or column of electrodes, respectively.

FIGS. 9a to 9c show plots of the change of threshold (dB) for all other single electrodes, half-rows of electrodes and columns of electrodes, as a function of distance (mm) from the best single electrodes, half-rows of electrodes or columns of electrodes, respectively. The results show that a cortical response may be achievable through application of current to half-rows or columns of electrodes at a greater distance from the best electrode(s), than is achievable through application of current to a single electrode. For example, referring to FIG. 9a, a cortical response was recorded upon application of current to a single electrode at a maximum of only 4 mm from the best single electrode. On the other hand, referring to FIG. 9c, a cortical response was recorded upon application of current to electrodes of a column of electrodes at distance of 7 mm from the best column of electrodes. In general, the best electrode, half-row of electrodes and column of electrodes, were all found to be located in the array adjacent the centre of the retina. Accordingly, at positions of the array located away from the centre of the retina, e.g., adjacent the periphery of the retina, simultaneous application of electrodes to lines of electrodes may be crucial, if a wide field of view for the patient is to be perceived.

Figure 8B:
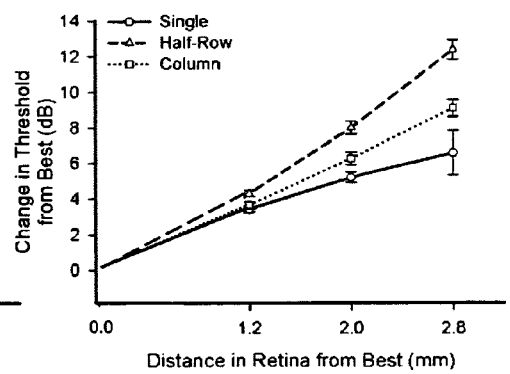
FIG. 8b shows a graph of exemplary mean changes in threshold (dB) for single electrodes, half-rows of electrodes and columns of electrodes, as a function of distance (mm) from a best single electrode, half-row of electrodes or column of electrodes.

FIG. 8b shows a graph of the mean change in threshold (dB) for single electrodes, half-rows of electrodes and columns of electrodes, as a function of distance (mm) from the best single electrode, half-row of electrodes or column of electrodes, respectively, and is derived from the plots shown in FIGS. 9a to 9c. Threshold change in dB is equal to 20 times the logarithm to base 10 of the ratio of the two thresholds being compared, either in charge per phase, or electric current for a fixed pulse width. As can be seen from the trend lines plotted in FIG. 8b, particularly at relatively small distances (up to 2.8 mm) from the best electrode(s), the threshold increases for half-rows and columns of electrodes more quickly, as a function of the distance from the best electrode(s), than for single electrodes. The greater steepness of the trend lines for half-rows and columns is indicative of their being less spreading (more localization) of the image perceived by the patient when current is applied simultaneously to electrodes of lines of electrodes, as opposed being applied to single electrodes only.

Figures 10A, 10B:
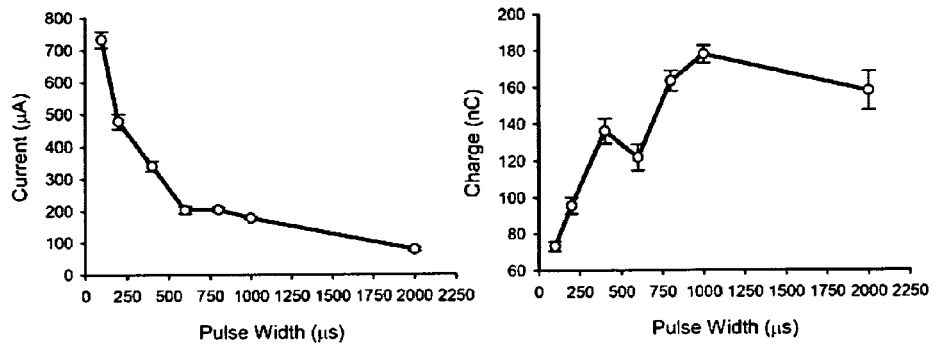
FIGS. 10a and 10b shows graphs of exemplary threshold current and threshold charge, respectively, for electrical stimulus applied to a single electrode as a function of pulse width.

With reference to FIGS. 10a and 10b, the effect of varying pulse width on threshold current and threshold charges was monitored for electrical stimuli applied via a single electrode. In this analysis, pulse widths of up to 2000 µs were considered, significantly higher than pulse widths up to 500 µs that were considered in the first example discussed with respect to FIG. 6. Referring to FIGS. 10a and 10b, although threshold current can be seen to decrease substantially exponentially for increasing pulse widths, the threshold charge can be seen to increase for pulse widths up to about 1000 µs. The results indicate that shorter pulses, e.g. less than 1000 µs, less than 750 µs or less than 500 µs, may be more charge efficient.

Figure 11A:
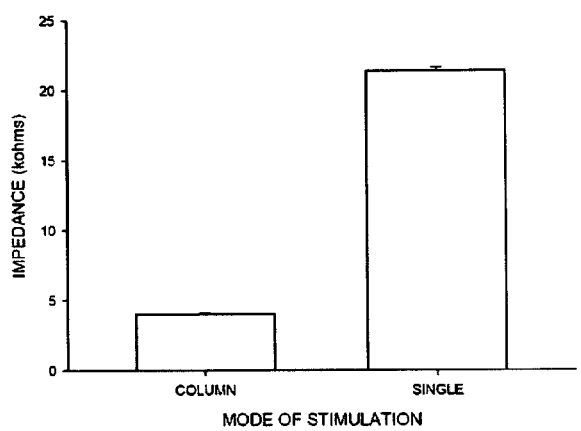
FIG. 11a shows a graph of exemplary electrical impedances for a column of 7 electrodes and for a single electrode.
Figure 11B:
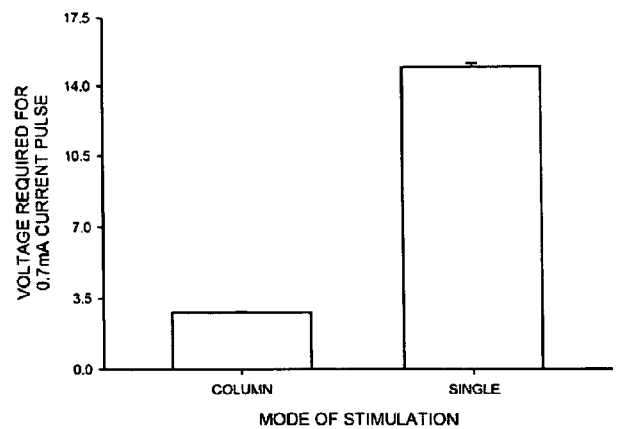
FIG. 11b shows a graph of exemplary voltages required to achieve a 0.7 mA current pulse for a column of 7 electrodes and for a single electrode.

Referring to FIG. 11a, the electrical impedance for both a column of 7 electrodes and a single electrode was determined. The column impedance was much lower than the impedance of the single electrode (approximately one quarter of the impedance). Since the column impedance was much lower than the single electrode impedance, with reference to FIG. 11b, the voltage required to apply a pulse having a particular current level (e.g. 0.7 mA), across the electrodes of the column simultaneously, was much lower than for the single electrode (approximately one quarter of the voltage). As discussed previously, the reduction in voltage required when current is applied simultaneously to electrodes of a line of electrodes can significantly lower power consumption, and voltage compliance requirements for the apparatus. Furthermore, this stimulation approach may allow electrodes that would normally be considered to have too high impedances to be used. For example, smaller electrodes may be used and/or electrodes of a particular type of high impedance material may be used than would otherwise be possible.

It is considered that the lower thresholds and higher localization of stimulation observed upon application of current to electrodes of lines of electrodes, as opposed to application of current to single electrodes, may be due to the line and orientation selectivity of cortical neurons and the different densities of retinal cells at the centre of the retina and at the periphery of the retina. Nonetheless, understanding the reasons for any of the observed phenomena discussed herein is not critical for gaining advantages of these phenomena, when using methods and apparatuses in accordance with aspects and embodiments of the present invention.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

The invention claimed is:

1. A method of electrically stimulating a patient's retina with an electrode array implanted in the patient's eye, the method comprising:
    capturing one or more images of a visual scene, including one or more objects located in the visual scene;
    detecting at least first and second lines and/or edges of the one or more objects in one of the one or more images;
    identifying a first line of electrodes in the electrode array corresponding to the detected first line and/or edge and identifying a second line of electrodes in the electrode array corresponding to the detected second line and/or edge,
    wherein the second line of electrodes is different from the first line of electrodes, the first and second lines of electrodes each comprising at least 3 electrodes;
    applying electrical current simultaneously to the at least 3 electrodes of the first line of electrodes to provide a visual percept to the patient of the entire detected first line and/or edge; and
    after applying electrical current simultaneously to the at least 3 electrodes of the identified first line of electrodes, applying electrical current simultaneously to the at least 3 electrodes of the second line of electrodes to provide a visual percept to the patient of the entire detected second line and/or edge.

2. The method of claim 1, wherein the line of electrodes comprises 4 or more electrodes.

3. The method of claim 1, comprising applying electrical current sequentially to different lines of electrodes corresponding to a plurality of lines and/or edges ranked in accordance with their visual importance to the patient.

4. The method of claim 1, wherein the electrical current is applied as one or more charge-balanced biphasic pulses with controlled pulse width and electric current dependent on the number of electrodes in the line of electrodes.

5. The method of claim 1, comprising determining a first region of the electrode array for stimulating a first region of the retina and a second region of the electrode array for stimulating a second region of the retina, wherein the identified first and second lines of electrodes are located in the second region of the electrode array, and wherein electrical current is additionally applied non-simultaneously to one or more single electrodes located in the first region of the electrode array.

6. The method of claim 5, wherein the locations of the first and second regions of the electrode array are determined based on the patient having substantially no visual perception response to the application of electrical current non-simultaneously to one or more single electrodes located in the second region of the electrode array, but having a visual perception response to the application of electrical current simultaneously to electrodes of one or more lines of electrodes in the second region of the electrode array.

7. The method of claim 1, wherein electrodes of the line of electrodes have a diameter of between 100 and 800 µm.

8. The method of claim 1, wherein the electrical current applied to the electrodes of the line of electrodes comprises charge balanced biphasic pulses, with a pulse width of less than or equal to 500 µs per phase.

9. An implantable component comprising,
    an electrode array; and an electrode interface, connectable to an image processor, the processor configured to detect at least first and second lines and/or edges of one or more objects in one or more captured images of a visual scene, the one or more objects being part of the visual scene, and identify a first line of electrodes in the electrode array corresponding to the detected first line and/or edge and identify a second line of electrodes in the electrode array corresponding to the detected second line and/or edge, wherein the second line of electrodes is different from the first line of electrodes, the first and second lines of electrodes each comprising at least 3 electrodes;

wherein the processor is configured to cause the electrode interface to apply electrical current simultaneously to the at least 3 electrodes of the first line of electrodes to provide a visual percept to the patient of the entire detected first line and/or edge, and, after applying electrical current simultaneously to the at least 3 electrodes of the identified first line of electrodes, apply electrical current simultaneously to the at least 3 electrodes of the second line of electrodes to provide a visual percept to the patient of the entire detected second line and/or edge.

* * * * *